United States Patent
Wan et al.

(10) Patent No.: US 7,459,425 B2
(45) Date of Patent: Dec. 2, 2008

(54) REAGENTS FOR PROTECTION OF PEPTIDE/PROTEINS CARBAMYLATION IN UREA SOLUTIONS UTILIZING NON-ETHYLENE-DIAMINE LIKE COMPOUNDS

(75) Inventors: Min Wan, Worcester, MA (US); Phillip Ropp, Chapel Hill, NC (US)

(73) Assignee: N.V. Organon (NL)

( * ) Notice: Subject to any disclaimer, the term of this patent is extended or adjusted under 35 U.S.C. 154(b) by 446 days.

(21) Appl. No.: 10/785,369

(22) Filed: Feb. 23, 2004

(65) Prior Publication Data

US 2004/0166572 A1 Aug. 26, 2004

Related U.S. Application Data

(60) Provisional application No. 60/449,091, filed on Feb. 21, 2003.

(51) Int. Cl.
*A61K 38/00* (2006.01)
*A61K 51/00* (2006.01)
*A61M 36/14* (2006.01)

(52) U.S. Cl. .......................................... 514/2; 424/1.69
(58) Field of Classification Search ....................... 514/2
See application file for complete search history.

(56) References Cited

U.S. PATENT DOCUMENTS 4,605,513 A 8/1986 DiMarchi .................... 530/303
2003/0045004 A1* 3/2003 Barri et al. ................... 436/518

OTHER PUBLICATIONS

Roberts et al. Ibuprofen, a putative anti-cataract drug, protects the lens against cyanate and galactose. Exp. Eye Res. vol. 50 (1990), pp. 157-164 (See document in related PCT/US2004/005374).*
Lewis et al. Bendazac prevents cyanate binding to soluble lens proteins and cyanate-induced phase-separation opacities in vitro:a poss. mechanism by which bendazac could delay cataract. Exp. Eye Res. vol. 43 (1986), pp. 973-979 (In PCT/US2004/00537).*
Crompton et al. Aspirin prevents carbamylation of soluble lens proteins and prevents cyanate-induced phase separation opacities in vitro:a poss. mechan. by which aspirin could prevent cataract. Exp. Eye Res.vol. 40 (1985),pp. 297-311 (In PCT/US2004/00537).*
International Search Report, No. PCT/US2004/005374, Nov. 22, 2004.
Hasuike et al., "Carbamylated Hemoglobin as a Therapeutic marker in Hemodialysis," Nephron, vol. 91, pp. 228-234 (2002).
Oimoni et al., "Carbamylation of Insulin and Its Biological Activity," Nephron, vol. 46, pp. 63-66 (1987).
Black et al., "Ion Chromatographic Determination of Cyanate in Saline Gold Processing Samples," Journal of Chromatography A, vol. 855, pp. 267-272 (1999).
Lippincott et al., "Carbamylation of Cysteine: A Potential Artifact in Peptide Mapping of Hemoglobins in the Presence of Urea," Analytical Biochemistry, vol. 267, pp. 57-64 (1999).
Marier et. al., "Determination of Cyanate, and a Study of its Accumulation in Aqueous Solutions of Urea," *Anal. Biochem 7* (1964) 304-314.
Stark, G.R., "Modification of Proteins with Cyanate," *Method In Enzymology 11* (1967) 590-594.
Stark et. al., "Reactions of the Cyanate Present in Aqueous Urea with Amino Acids and Proteins," *J. Biol. Chem. 235* (1960) 3177-3181.
Crompton et al., "Aspirin Prevents Carbamylation of Soluble Lens Proteins and Prevents Cyanate-induced Phase Separation Opacities In Vitro: A Possible Mechanism by which Aspirin could Prevent Cataract," *Exp. Eye Res. 40* (1985) 297-311.

* cited by examiner

*Primary Examiner*—Cecilia Tsang
*Assistant Examiner*—Maury Audet
(74) *Attorney, Agent, or Firm*—Susan Hess; F. Aaron Dubberley

(57) ABSTRACT

The present invention generally relates to non-ethylene diamine like compounds that prevent and/or delay carbamylation of peptides.

13 Claims, No Drawings

REAGENTS FOR PROTECTION OF PEPTIDE/PROTEINS CARBAMYLATION IN UREA SOLUTIONS UTILIZING NON-ETHYLENE-DIAMINE LIKE COMPOUNDS

RELATED APPLICATIONS

This application claims priority to provisional application No. 60/449,091, filed on Feb. 21, 2003 and titled "Reagents for Protection of Peptide/proteins Carbamylation in Urea Solutions Utilizing Non-Ethylene-diamine Like Compounds."

FIELD OF THE INVENTION

Embodiments of the present invention generally relate to a class of molecules that substantially prevent the carbamylation of peptides.

BACKGROUND OF THE INVENTION

It has been recognized for many years that cyanate readily reacts with certain amino acid side chain functional groups of a peptide [see G. R. Stark, Method In Enzymology 11, 590-594 (1967)].

Urea-containing solutions are commonly used to solubilize proteins. One of the disadvantages of the use of urea is that it can dissociate into cyanic acid. The cyanate thus formed often reacts with the primary amine in the protein to yield a carbamylated derivative. This derivative may have biological and antigenic properties that are different from those of the native protein. As a result that the therapeutic efficacy of a carbamylated protein may be compromised. In addition, irreversible carbamylation of primary amines on proteins or peptides could complicate the purification process and/or reduce the biological activities of therapeutic bioproducts.

At equilibrium, an 8 M urea solution may contain 0.02 M cyanate, according to the following reaction:

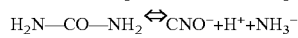
$H_2N\text{—}CO\text{—}NH_2 \Leftrightarrow CNO^- + H^+ + NH_3^-$

The nonspecific, pH dependent binding reaction between cyanic acid and protein is called carbamylation:

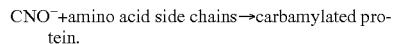
$CNO^- + \text{amino acid side chains} \rightarrow \text{carbamylated protein}.$ The cyanate reaction with —$NH_2$ side chains is irreversible and has an appreciable rate. Also, slightly acidic conditions promote a rapid reaction of cysteine sulfhydryls with residual cyanate derived from urea. However, the carbamylation of the —SH and —imidazole side chains is reversible in slightly alkaline pH. The carbamylated residues are neutral, so that the proteins become less charged and can be reflected in their ion exchange chromatographic behavior.

Protein carbamylation is a major issue both in vivo and in vitro. Lippincott and Apostol (1999) have shown that hemoglobins had a significant level of carbamylated cysteines as an artifact of protein digestion in the presence of urea. Hasuike et al. (2002) have recently shown that cyanate can induce hemolysis by carbamylation of erythrocytes. Thus, carbamylated hemoglobin serves as a marker of posttranslational protein modification associated with such uremic complications as atherosclerosis. Oimomi et al. (1987) measured the activity of carbamylated insulin and showed that both immunological and biological activities changed. In addition, Crompton et al. (1985) had shown that the carbamylation of lens proteins by cyanate causes conformational changes that lead to cataracts. In vitro, the carbamylation of proteins results in lower protein solubility and biological activity, that can lead to a low purification yield and a difficult purification process.

Different methods to prevent carbamylation have been proposed. Lowering the temperature slows down both the cyanate formation and subsequent carbamylation, but increases the viscosity that can impact downstream processes such as filtration and chromatography. Deionization of urea solution only temporarily removes the cyanate from solution. Lowering the pH to 2 decreases cyanate formation but is unattractive for most proteins. Amine-specific derivatization and deprotection is not a convenient quantitative approach. While these approaches have applications in special circumstance, none can be generally applied in the field.

Since cyanate formation in the urea buffer cannot be prevented under the condition of normal protein purification, an alternative approach would be to remove cyanate as it forms. A search for $CNO^-$ scavengers has been reported (e.g. $H_2N\text{—}CH_2\text{—}CH_2\text{—}NH_2$ for insulin, see DiMarchi patent, 1986). A good protection agent is considered to be inexpensive, inert, soluble, and readily removable. It has to provide high level of protection, and possibly form irreversible complexes with HOCN at neutral pH. Scavenger design is difficult because each functional group has different reactivity, and the protection mechanism is not clear. Good candidates could be amines that are more reactive with $CNO^-$ than the primary amine groups of proteins, and have more than one functional group that are sterically unhindered for faster kinetics.

Two alternatives which can be considered for diminishing losses due to carbamylation are addition of a protective scavenger and reversible amine protection. While the latter approach may permit complete protection it is not always desirable due primarily to the difficulty in achieving quantitative amine-specific derivatization and deprotection. If an appropriate reaction scavenger is available, its utilization is a more desirable and less expensive and demanding alternative to reversible protection. An ideal scavenger, of course, is one that is inexpensive and that provides complete protection from modification while otherwise being totally inert to all other reaction components. Since proteins contain a wide range and diversity of functional groups, each of which possesses a different reactivity toward a particular reagent, it is difficult a priori to predict an effective scavenger. While carbamylation is most rapid at sulfhydryl and imidazole sites, the resulting reaction products are of little concern due to their rapid reversal in slightly alkaline buffers. Modification of peptidyl primary amines (for example, $NH_2$-terminus and lysine residues) occurs at an appreciable rate and, for all practical purposes, is irreversible [see G. R. Stark, W. H. Stein, and S. Moore, J. Biol. Chem. 235,-3177-3181 (1960)]. At each site of primary amine carbamylation the peptide is reduced in physiological buffers one positive charge, thereby often resulting in diminished peptidyl solubility and/or biological activity. Since cyanate is an equilibrium product of aqueous urea solutions [see J. R. Marier and D. Rose, Anal. Biochem. 7, 304-314 (1964)], all peptides containing reactive functional groups, when handled in the presence of urea, are susceptible to irreversible carbamylation. Urea, being an excellent peptidyl solvent due to its ability to disaggregate structural order, facilitates carbamylation. These undesirable derivatized forms not only represent immediate losses in yield but also constitute complications in purification processes.

To diminish carbamylation of peptides in many prior art urea solutions, the solutions were freed of cyanate prior about immediately prior to use, and all chemical manipulations were conducted at reduced temperatures.

There are several prior art methods and/or processes for the removal of cyanate from mediums and/or solutions. One process, the removal of cyanate by deionization, or through pH reduction to below 2.0, is at best temporary, since ammonium cyanate reappears as an equilibrium product of aqueous urea. As well, the low temperature operational restriction results in slower chemical reactions and complicated operations.

The DiMarchi process, and especially the '513 patent, teaches that if an effective scavenger is to be found, it is important first to determine the optimum conditions for carbamylation. In fact, it was the DiMarchi process that aided in the understanding that there are more than one reactive species when considering the carbamylation of proteins during synthesis. It is commonly understood in the art that if cyanate is the reactive species, the rate of reaction should increase with increasing pH until a limit is reached at a pH slightly above the pKa of the amine. However, if cyanic acid is the reactive entity, the relative rate of reaction with an amine should be biphasic with a pH optimum of approximately 6.5. DiMarchi further taught that an ideal reagent for use in preventing peptide carbamylation (scavenge) during synthesis would have the characteristics of being inert to peptides, capable of forming irreversible complexes with cyanic acid at approximately pH 6.5.±2.0, and be a 1,2-ethylene diamine-like compounds or a compound structurally related to 1,2-ethylene diamine and having some carbamylation inhibition and/or reduction characteristics similar thereto. The DiMarchi process defines a compound structurally related to 1,2-ethylene diamine like compound as:

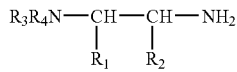

In which $R_1$, $R_2$, $R_3$, and $R_4$ are groups which, as a composite, do not exert significant changes (1) in the pKa values and (2) in the steric accessibility of the respective amino acid groups relative to the properties of 1,2-ethylene diamine itself. DiMarchi stresses that it is the steric arrangement of the 1,2-ethylene diamine like compound that provide for the scavenging ability.

However, while the 1,2-ethylene diamine like compounds possess good cyanate scavenging ability, they are highly basic and strongly influence pH and buffering capacity when used at the concentration suggested by DiMarchi. Therefore the artfield is in search of other compounds and/or groups of compounds that function as carbamylation inhibitors without this disadvantage of the 1,2-ethylene diamine like compounds. Such compounds should either be much more effective scavengers than 1,2-etylene diamine, so that they can be used in sub-milimolar concentration, or significantly less basic than 1,2-ethylene diamine, preferably with low or no net charge at the experimental conditions, having low impact on the buffering capacity of typical biological buffers when used at a milimolar concentrations. Alternatively, such compounds would have a buffering capacity within or close to the neutral range and could be used as buffers.

SUMMARY OF THE INVENTION

Embodiments of the present invention generally relate to a class of non-ethylene diamine like compounds that are capable of substantially inhibiting and/or delaying carbamylation of peptides. In particular, various embodiments of the present invention relate to compounds that provide protection to proteins from carbamylation in the presence of cyanate and/or in a urea buffer.

Using bovine pancreatic ribonuclease (RNase A) as a model protein, it has been found that several non-ethylene diamine like compounds, such as glycinamide, histidine, 4-hydroxyl proline and some dipeptides, such as Glycine-Glycine (Gly-Gly), and Glycine-Histidine (Gly-His), significantly inhibited carbamylation of RNase A. Unexpectedly, these compounds are not 1,2-ethylene diamine like compounds and are not expected to act as carbamylation inhibitors as defined in the DiMarchi process.

DETAILED DESCRIPTION OF THE INVENTION

As used herein, the term "ethylene diamine like compounds" means and refers to a compound structurally related to, or like, 1,2-ethylene diamine and having some carbamylation inhibition and/or reduction characteristics similar thereto.

The processing of peptides as contemplated herein encompasses any of a wide range of peptide processing. Typical, non-limiting, examples are purification, chemical modification, including, e.g., peptide sulfitolysis, and other such peptide processing steps.

Accordingly, in an embodiment, the present invention comprises a process for inhibiting and/or delaying carbamylation of a peptide/protein in a urea and/or cyanate containing solution during processing of said peptide/protein comprising the step of adding a carbamylation inhibiting compound to the process wherein said compound is not an ethylene diamine like compound.

In an embodiment, the compound is selected from the group consisting of glycinamide, histidine, 4-hydroxyl proline, Glycine-Glycine (Gly-Gly), and Glycine-Histidine (Gly-His).

Generally, the concentration of the scavenger compound used in the process of this invention is within the range from about 1 mM to about 150 mM. In an embodiment, the concentration of the compound is within the range from about 10 mM to about 100 mM, based upon the total processing medium. In another embodiment, the concentration of the compound is within the range from about 25 mM to about 50 mM. However, the concentration of the compound may vary according to the concentration of the cyanate in solution.

Carbamylation inhibition during processing is available for essentially any peptide and/or protein, irrespective of structure, when subjected to conditions in which amounts of cyanic acid can be expected to be present. Thus, for example, and not by way of limitation, peptides/proteins such as ribonucleases, insulin A-chain, insulin B-chain, proinsulin, C-peptide, pancreatic polypeptide, growth hormone, growth hormone releasing factor, insulin-like growth factor, somatostatin, and, others are suitable for use with the novel non-ethylene diamine like compounds of the present invention. Preferred peptides/proteins are soluble in urea and readily carbamylate in the presence of urea.

The compounds described in this invention do not possess the diamine functionality characteristic of ethylene diamine-like compounds described by DiMarchi, and exhibit much lower net charge at neutral pH making them superior to ethylene-diamine-like compounds as buffer additives. In an embodiment, the compound is selected from the group consisting of glycinamide, histidine, 4-hydroxyl proline, Glycyl-Glycine (Gly-Gly), and Glycine-Histidine (Gly-His). Surprisingly, the compounds selected from this group show comparable cyanate-scavenging and carbamylation-protecting properties to ethylene diamine while lacking the diamine functionality. Unexpectedly, it has been further observed, that some of the cyanate scavenging compounds described in the current invention do not possess any primary amine or sulf-hydryl functionality while still showing the ability to scavenge cyanate and protect against carbamylation, the examples being diethanolamine and hydroxyproline.

Further unexpectedly, it has been found that it is not necessary or required that the compound be sterically unhindered as proposed by DiMarchi for the compound to function as a cyanate scavenger. Compounds selected from a group of non-ethylene diamine like compounds that varied sterical constrains around the amino group inhibit and/or delay carbamylation of peptides/proteins with comparable results. In an embodiment, the compound is selected from the group consisting of glycinamide, histidine, 4-hydroxyl proline, Gycine-Glycine (Gly-Gly), and Glycine-Histidine (Gly-His).

The structures of the compounds are as follows:

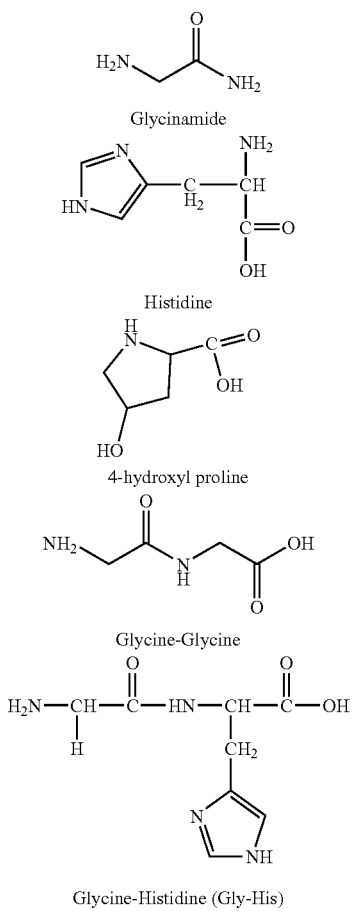

As can be seen, when compared to ethylene diamine like compounds,

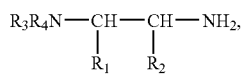

selected compounds of the present invention, such as 4-hydroxyproline or diethanolamine containing a secondary amine group, cannot be referred to as sterically unhindered. Therefore, it is proposed that the effectiveness of the compounds of the present invention is determined by the stability of a cyanate-scavenger adduct rather than any sterical constrains within the scavenger itself. Such compounds include but are not limited to 4-hydroxyproline, histidine, histidine-glycine, and diethanolamine, consequently, the effectiveness of the compounds described in the present invention can not be predicted from the worked described by DiMarchi.

In another surprising fact, the pKa value(s) of the amino group of a compound may vary significantly from the pKa of an ethylene diamine like compounds while still retaining a good ability to inhibit and/or delay the carbamylation of peptides/protein during processing. DiMarchi proposed that the low pK of approximately 7.5 of one of the amino groups of ethylene diamine or ethylene diamine-like compounds was essential for good scavenger properties. In various embodiments of the present inventionan amine may be used with a pKa of about 8.20. Notably, such a mono-amine compounds would not be predicted to function as carbamylation inhibitors and/or delayors, a suitable example being glycineamide and/or glycine-glycine. In another embodiment, three groups having varying pKa values of about 1.82, about 6.04 and about 9.33, a suitable example being Histidine with a —COOH, a NH.sub.2, and a side chain. In another embodiment, two groups with pKa values of about 1.92 and about 9.73, a suitable example being hydroxy-proline.

As defined above, embodiments of the present invention encompass numerous processes to which peptides/proteins are subjected. In an embodiment, the process is solubilizing the peptide/protein in urea. In another embodiment, the process is purification of peptide/protein. However, the invention may comprise other processes.

Various embodiments of the present invention inhibit carbamylation of the peptide/protein to varying degrees. In an embodiment, the carbamylation percent protection is about 100% after three weeks. In another embodiment, the compound inhibits carbamylation of ribonuclease A to a greater extent than does 1,2-ethylene diamine inhibit the carbamylation of ribonuclease A. Preferred compounds for comparison comprise a compound selected from the group consisting of histidine, 4-hydroxyl proline, and Gly-Gly.

While the invention has been described in connection with specific embodiments thereof, it will be understood that it is capable of further modifications and the appended. Claims are intended to cover any variations, uses, or adaptations of the invention following, in general, the principles of the invention and including such departures from the present disclosure as come within known or customary practice within the art to which the invention pertains and as may be applied to the essential features herein before set forth whether now existing or after arising. Further, while embodiments of the invention have been described with specific dimensional characteristics and/or measurements, it will be understood that the embodiments are capable of different dimensional characteristics and/or measurements without departing from the principles of the invention and the appended Claims are intended to cover such differences. Furthermore, all patents and other publications mentioned herein are herby incorporated by reference.

EXAMPLES

In this experiment, a series of amines, amides, amino acids, and di- and tri-peptides were tested and compared with 1,2 ethylene diamine, and their efficiency quantified as % protection against RNase A carbamylation. In our study on cyanate scavengers for protein carbamylation protection, bovine pancreas RNase A (124 amino acid residues, ~14 kDa) served as the model protein. It is a notably stable enzyme that may be inactivated by long exposure at moderate temperature to urea ($CNO^-$) by chemical changes at the 8 Cys, 10 Lys, 4 Arg, 4 His residues.

Materials and Methods

Cyanate Carbamylation Study

A 2 mg/ml stock solution of bovine RNase A (Sigma), a 100 mM stock solution of sodium cyanate (Sigma), and a stock solution of 250 mM sodium phosphate pH 7.9 were prepared in water and stored at −70° C. The tested scavengers (Table 1) were prepared in 0.5 M stock concentrations, adjusted to pH 8 using HCl or NaOH, and stored at room temperature. The pH of the histidine solution was not adjusted (it could not be adjusted properly). Due to solubility limitation, a 0.2 M stock solution was made for GlyGlyGly, tryptophan, melamine, triaminopyrimidine, and indole. All amino acids were the L isomer.

RNase A, at 1 mg/ml, was carbamylated by incubation with cyanate at room temperature. Different scavenger concentrations (100, 50, 10 and 5 mM) were tested for protective potential. The final concentrations of other components in the carbamylation reaction mixture were 5 mM for $CNO^-$ and 50 mM sodium phosphate pH 7.9.

The controls were added to each reaction setup: A negative control, which had neither cyanate nor scavenger, was used for quantifying the RNase natural decay. A positive control, which had 5 mM cyanate, but no any scavenger reagent, was used for estimating the completion of the carbamylation reaction.

In all experiments, 5 mM cyanate was added last.

Non-carbamylated RNase A was quantitatively determined by HPLC on a Mono S column (Amersham Biosciences, Piscateway, N.J.). Aliquots of the carbamylation reaction mixture were taken at 0, 3, 7, 14, 21 day time points, and the samples were analyzed by HPLC. If not used immediately, the samples were frozen at −70° C. Prior to HPLC, the samples were titrated to pH 5 using 38% acetic acid solution to a final 1:1 dilution. A buffer system consisting of 50 mM ammonium acetate pH 5 (buffer A) and 1 M ammonium acetate pH 5 (buffer B) was used for separation of carbamylated and non-carbamylated RNase species. A gradient was used from 10% B to 70% B over 14 min. Then the column was washed with 70% buffer B for 2 min. At 16 min the mobile phase was switched back to 10% B to equilibrate the system before next injection. All chromatographic separations were carried out at 10° C., using a mobile phase flow rate of 1 ml/min, and 100 μl sample injection volume.

The amount of remaining non-carbamylated RNase A in the test was converted to percent carbamylation protection. To account for differences in samples, time 0 of each tested group was considered to be 100% protection based on the assumption that there is no carbamylation at time point 0. The data were further corrected point-by-point for natural protein decay.

Cyanate Assay

To check for CNO-/scavenger interaction and estimate reaction kinetics, the same reaction setup was used, but no protein was added to final mixture. Aliquots were taken at 2 h and 24 h time points and treated as above. A modified HPLC procedure (Black & Schulz, 1999) was used for free cyanate detection. The HPLC samples were diluted 1:20 with water. Separations were carried out at room temperature, using a mobile phase flow rate of 1.2 m/min and 100 μl injection volume. The results were normalized to 5 mM, the starting cyanate concentration. In some cases, the scavenger peak overlaps the cyanate peak, so the integration values are smaller than expected.

Urea Carbamylation Assay

A 9 M urea (JT Baker) stock solution was made fresh in 50 mM sodium phosphate, pH 7.9, and used immediately to make up a 1.1 mg/ml RNase A stock solution. The final urea concentration in the carbamylation mixture was 8.1 M and the RNase A was 1 mg/ml. No sodium cyanate added to the reaction mixture. The experiment further proceeded as described in cyanate carbamylation study.

Results and Discussion

Cyanate Carbamylation Study

Table 1 summarizes all compounds tested for their potential protection against RNase A carbamylation by cyanate. The percent protection of RNase A was determined for 100 mM tested reagents after three weeks in the presence of 5 mM cyanate. The 5 best possible protection reagents, which showed a higher than 90% protection level, were glycinamide, L-Histidine, hydroxyl-Proline, glycylglycine and glycylhistidine. The time and concentration dependence of these compounds on RNase A carbamylation is shown in Table 2. In the table, the positive control was set with RNase A, 5 mM cyanate, but without any potential protection reagents. The negative control was only the RNase A in test buffer. Data from Table 2 clearly proved that the carbamylation of RNase A by cyanate was inhibited with 50 or 100 mM tested reagents, compared to the positive control.

TABLE 1

Tested compounds in the carbamylation experiment. The percent protection was determined for 100 mM scavenger after 3 weeks in the presence of 5 mM cyanate.

| Tested Compound | Carbamylation protection (%) |
| --- | --- |
| 1,2-Ethylene diamine | 99 |
| Ethanolamine | <70 |
| Diethanolamine | 82 |
| Taurine | <70 |
| L-Glycine | 77 |
| Glycinamide | 93 |
| L-Lysine | 77 |
| L-Arginine | 77 |
| Putresceine (Tetramethylenediamine) | <70 |
| L-Histidine | 100 |
| Histamine (2-(4-imidazolyl)-ethylamine) | <70 |
| Imidazole | <70 |
| L-Trptophan | <70 |
| Indole | <70 |
| L-Proline | <70 |
| HO-Proline (trans-4-hydroxy-L-proline) | 100 |
| Gly-Gly | 100 |
| Gly-His | 95 |
| His-Gly | 85 |
| Gly-Gly-Gly | 77 |
| Melamine (2,4,6-triamino-1,3,5 triazide) | <70 |
| 2,4,6-triamino pyrimidine | <70 |

TABLE 2

Selected results of RNase cyanate carbamylation study.

| Tested compounds and concentration | | Carbamylation Protection (%) | | | | |
|---|---|---|---|---|---|---|
| | | Day 0 | Day 3 | 1 week | 2 week | 3 week |
| 1,2-Ethylene diamine | 100 mM | 100 | 98 | 96 | 96 | 93 |
| | 50 mM | 100 | 94 | 93 | 93 | 90 |
| L-Histidine (His) | 100 mM | 100 | 93 | 97 | 102 | 102 |
| | 50 mM | 100 | 68 | 70 | 76 | 77 |
| Glycinamide (GLA) | 100 mM | 100 | 97 | 96 | 94 | 93 |
| | 50 mM | 100 | 93 | 92 | 92 | 87 |
| Glycyl-glycine (GlyGly) | 100 mM | 100 | 98 | 98 | 100 | 101 |
| | 50 mM | 100 | 91 | 92 | 94 | 93 |
| Gly-His (GlyHis) | 100 mM | 100 | 97 | 95 | 97 | 95 |
| | 50 mM | 100 | 95 | 95 | 96 | 91 |
| Hydroxy-Proline (HO-Pro) | 100 mM | 100 | 104 | 102 | 98 | 103 |
| | 50 mM | 100 | 102 | 101 | 102 | 100 |
| Positive control (PC) | | 100 | 36 | 16 | 11 | 11 |
| Negative control (NC) | | 100 | 94 | 93 | 89 | 89 |

Cyanate Scavenging Study

In order to verify the mechanism of the carbamylation protection by the tested compounds, a cyanate level test was performed for 5 mM cyanate in the presence of the above listed compounds and compounds with similar structure, such as diethanolamine, di-peptide HisGly, and tri-peptide GlyGlyGly. Table 3 shows the results of cyanate scavenging study. The protection was calculated based on the percent cyanate remaining from the starting concentration at 2 hr and 24 hr time points. All tested compounds showed over 50% cyanate scavenging capability after 24 hr at the concentration of 25 mM or greater, except the diethanolamine. At compound concentrations below 10 mM, the cyanate scavenging potential was not conclusive. The data agreed well with the results of cyanate carbamylation protection study on RNase A. Based on these results, the mechanism of the carbamylation protection on RNase A could be attributed to the cyanate scavenging.

TABLE 3

Results of cyanate scavenging.

| Tested Reagents | Time | CNO⁻ Remaining (%) | | | | |
|---|---|---|---|---|---|---|
| | | 100 mM | 50 mM | 25 mM | 10 mM | 5 mM |
| 1,2-Ethylene diamine | 2 h | 20.0 | 45.0 | NA | 67.6 | 74.6 |
| | 24 h | 0 | 2.5 | 16.4 | 43.8 | 87.8 |
| Diethanolamine (DEA) | 2 h | 45.4 | 92.1 | 87.5 | 78.2 | 78.8 |
| | 24 h | 5.5 | 4.2 | 59.6 | 79.7 | 75.3 |
| Glycylglycine (GlyGly) | 2 h | 23.1 | 66.4 | 80.1 | 79.3 | 82.7 |
| | 24 h | 0 | 3.0 | 11.9 | 42.4 | 64.1 |
| L-Histidine (His) | 2 h | 22.9 | 73.2 | 91.0 | 49.5 | 85.1 |
| | 24 h | 2.0 | 10.9 | 32.5 | 59.6 | 79.9 |
| Glycinamide (GLA) | 2 h | 29.5 | 49.5 | 80.2 | 70.9 | 78.7 |
| | 24 h | 2.2 | 4.4 | 19.0 | 0.9 | 65.7 |
| His-Gly (HisGly) | 2 h | 39.5 | 52.8 | 70.9 | 28.6 | 81.4 |
| | 24 h | 5.0 | 20.2 | 31.5 | 60.4 | 81.7 |
| Gly-His (GlyHis) | 2 h | 37.1 | 49.2 | 76.7 | 63.0 | 86.2 |
| | 24 h | 0.8 | 6.9 | 20.9 | 50.9 | 77.6 |
| GlyGlyGly (GGG) | 2 h | 42.2 | 52.6 | 68.9 | 50.9 | 1.2 |
| | 24 h | 1.1 | 4.6 | 11.5 | 81.5 | 34.1 |
| Hydroxy-proline (HO-Pro) | 2 h | 38.2 | 40.9 | 61.2 | 64.4 | 61.5 |
| | 24 h | 1.1 | 8.5 | 26.6 | 57.2 | 72.2 |

Urea Carbamylation Study

In this experiment, urea in the process buffer was the cause of carbamylation during protein purification. Cyanate accumulation in the urea buffer is a gradual process. To demonstrate that the cyanate scavengers is generally applicable to prevent protein carbamylation during purification, a urea carbamylation study was performed on RNase A. The urea carbamylation study was set with 1 mg/ml RNase A in 8M urea buffer, pH 7.9 containing different concentration of scavenger reagents over a period of three weeks. The results of this experiment are summarized in Table 4. The data showed that all tested scavengers were able to protect RNase A against the carbamylation to some degree. The trend was the same as observed in cyanate carbamylation study, however, the degrees of protection observed were consistently lower than those observed from the direct cyanate carbamylation study. There could be two possible explanations for this discrepancy: the kinetics might be different in urea, and/or RNase A is unfolded in urea, so more sites are exposed for carbamylation. The recommended scavenger concentration for preventing RNase A carbamylation is 25 mM or greater.

TABLE 4

Results of RNase A urea carbamylation study.

| Tested reagents And the concentration | | Protection of carbamylation in urea (%) | | | | |
|---|---|---|---|---|---|---|
| | | Day 0 | Day 3 | 1 week | 2 week | 3 week |
| 1,2-Ethylene diamine | 50 mM | 100 | 83 | 62 | 65 | 54 |
| | 25 mM | 100 | 88 | 63 | 61 | 53 |
| | 10 mM | 100 | 83 | 60 | 50 | 37 |
| L-Histidine (His) | 50 mM | 100 | 101 | 98 | 91 | 80 |
| | 25 mM | 100 | 85 | 67 | 41 | 30 |
| | 10 mM | 100 | 84 | 43 | 22 | 16 |
| Glycinamide (GLA) | 50 mM | 100 | 83 | 66 | 60 | 51 |
| | 25 mM | 100 | 85 | 64 | 56 | 46 |
| | 10 mM | 100 | 81 | 58 | 39 | 29 |
| Glycylglycine (GlyGly) | 50 mM | 100 | 92 | 76 | 64 | 60 |
| | 25 mM | 100 | 88 | 71 | 56 | 50 |
| | 10 mM | 100 | 59 | 62 | 44 | 32 |
| His-Gly (HisGly) | 50 mM | 100 | 88 | 67 | 66 | 63 |
| | 25 mM | 100 | 82 | 64 | 52 | 43 |
| | 10 mM | 100 | 82 | 51 | 38 | 27 |
| Gly-His (GlyHis) | 50 mM | 100 | 88 | 69 | 63 | 53 |
| | 25 mM | 100 | 86 | 61 | 49 | 46 |
| | 10 mM | 100 | 84 | 58 | 38 | 27 |
| GlyGlyGly (GGG) | 50 mM | NA | NA | NA | NA | NA |
| | 25 mM | 100 | 85 | 62 | 49 | 43 |
| | 10 mM | 100 | 85 | 61 | 42 | 28 |
| Hydroxy-proline (HO-Pro) | 50 mM | 100 | 90 | 69 | 55 | 50 |
| | 25 mM | 100 | 86 | 53 | 47 | 39 |
| | 10 mM | 100 | 80 | 52 | 31 | 24 |
| Control | 0 mM | 100 | 86 | 33 | 13 | 11 |

Conclusions

Some compounds, have the potential to prevent protein carbamylation. Compounds, such as L-Histidine, glycinamide, hydroxyl-proline, di-peptides GlyGly, GlyHis and His-Gly, as well as tri-peptide GlyGlyGly, showed significant protection to carbamylation of RNase A. The protection of RNase A by the tested compounds is concentration dependent, with most compounds proficient at 25 mM or greater. RNase A in that about 20% of the amino acid residues of RNase A are susceptible to carbamylation, serves as an excellent model protein for the this study. The concentration of scavenger could vary, depending on the available carbamylation sites of the target protein. Based on the data collected, the cyanate scavengers tested here can be used in protein purification processes.

REFERENCES

Crompton M, Ixon K C, Harding J J. *Exp. Eye Res.* 1985, 40: 297-311. Aspirin prevents carbamylation of soluble lens proteins and prevents cyanate-induced phase separation opacities in vitro: a possible mechanism by which aspirin could prevent cataract.

DiMarchi, R D UD Patent 4605513, 1986. Eli Lilly co. Process for inhibiting peptide carbamylation.

Hasuike Y, Nakanishi T, Maeda K, Tanaka T, Inoue T, Takamitsu Y. *Nephron* 2002, 91: 228-234. Carbamylated hemoglobin as a therapeutic marker in hemodialysis.

Lippincott J, Apostol I. *Anal. Biochem.* 1999, 267: 57-64. Carbamylation of cysteine: a potential artifact in peptide mapping of hemoglobins in the presence of urea.

Oimomi M, Hatanaka H, Yoshimura Y, Yokono K, Baba S, Taketomi Y. *Nephron* 1987, 46: 63-6. Carbamylation of insulin and its biological activity.

Black S B and Schulz R S. *J. Chrom. A.* 1999, 855: 267-272. Ion chromatography determination of cyanate in saline gold processing samples.

What is claimed is:

1. A process for inhibiting and/or delaying carbamylation of a polypeptide in a urea and/or cyanate containing solution, the process comprising a step of adding a carbamylation-inhibiting compound to the solution, wherein said carbamylation-inhibiting compound is glycinamide.

2. The process of claim 1, wherein the polypeptide is a ribonuclease.

3. The process of claim 2, wherein the ribonuclease is RNase A.

4. The process of claim 1, wherein the carbamylation-inhibiting compound is added to the solution in an amount effective to provide about 100% carbamylation protection of the polypeptide for a period of three weeks.

5. The process of claim 1, wherein the concentration of the carbamylation-inhibiting compound is between 1 mM and 150 mM.

6. The process of claim 5, wherein the cyanate in the solution is at a concentration of about 5 mM.

7. The process of claim 1, wherein the carbamylation-inhibiting compound has a buffering capacity of about neutral.

8. A process for inhibiting and/or delaying carbamylation of a polypeptide in a urea and/or cyanate containing solution, the process comprising a step of adding a carbamylation-inhibiting compound to the solution, wherein the carbamylation-inhibiting compound is a dipeptide selected from the group consisting of Glycine-Glycine (Gly-Gly) and Glycine-Histidine (Gly-His).

9. The process of claim 8, wherein the dipeptide is Glycine-Glycine (Gly-Gly).

10. A process for inhibiting and/or delaying carbamylation of a polypeptide in a urea and/or cyanate containing solution, the process comprising a step of adding a carbamylation-inhibiting compound selected from the group consisting of histidine and 4-hydroxyl proline to the solution, wherein the carbamylation-inhibiting compound is added to the solution in an amount effective to provide about 100% carbamylation protection of the polypeptide for a period of three weeks.

11. The process of claim 8, wherein the concentration of the carbamylation-inhibiting compound is between 1 mM and 150 mM.

12. The process of claim 11, wherein the cyanate in the solution is at a concentration of about 5 mM.

13. The process of claim 8, wherein the carbamylation-inhibiting compound has a buffering capacity of about neutral.

* * * * *